United States Patent
Haga et al.

(10) Patent No.: US 7,323,705 B2
(45) Date of Patent: Jan. 29, 2008

(54) LIQUID LEVEL MEASUREMENT

(75) Inventors: Douwe D. Haga, Redwood City, CA (US); Michael R. Flatbush, San Ramon, CA (US); Michael Mosseau, Santa Clara, CA (US); Tony S. Yan, Millbrae, CA (US); Willy Wiyatno, Union City, CA (US); Mark T. Reed, Menlo Park, CA (US)

(73) Assignee: Applera Corporation, Foster City, CA (US)

( * ) Notice: Subject to any disclaimer, the term of this patent is extended or adjusted under 35 U.S.C. 154(b) by 64 days.

(21) Appl. No.: 11/130,606

(22) Filed: May 16, 2005

(65) Prior Publication Data

US 2005/0285060 A1 Dec. 29, 2005

Related U.S. Application Data

(60) Provisional application No. 60/584,450, filed on Jun. 29, 2004, provisional application No. 60/664,730, filed on Mar. 24, 2005.

(51) Int. Cl.
  *G01N 21/49* (2006.01)
  *G01N 21/85* (2006.01)
  *G01N 15/06* (2006.01)
(52) U.S. Cl. .................. 250/577; 356/624; 73/293
(58) Field of Classification Search .............. 250/577, 250/900–908, 201.2, 201.3; 356/624, 436, 356/627; 73/1.73, 1.74, 290 R, 291, 293; 340/618, 619
See application file for complete search history.

(56) References Cited

U.S. PATENT DOCUMENTS

| 5,880,364 A | 3/1999 | Dam |
| 6,443,022 B1* | 9/2002 | Gordon .................... 73/864.25 |
| 2003/0038950 A1* | 2/2003 | Spolaczyk .................. 356/624 |
| 2004/0022689 A1 | 2/2004 | Wulf et al. |

FOREIGN PATENT DOCUMENTS

| EP | 0 615 607 A | 9/1994 |
| EP | 0 842 441 B1 | 4/2002 |
| JP | 2001-90733 A | 4/2001 |

OTHER PUBLICATIONS

International Search Report from Int'l application No. PCT/US2005/023435, mailed Nov. 4, 2005; along with Written Opinion of the ISA.
*High-Accuracy Surface Scanning Method*, 10 page brochure for new Surface Scanning Laser Confocal Displacement Meter, Keyence Corporation of America, Woodcliff Lake, NJ, www.keyence.com, 2004.
*Laser Confocal Displacement Meters*, LT Series, pp. 398-405, Keyence Corporation of America, Woodcliff Lake, NJ, www.keyence.com.
*Laser Confocal Displacement Meter*, LT Series, Instruction Manual, pp. i-59, Keyence Corporation, www.keyence.com.

* cited by examiner

*Primary Examiner*—Georgia Epps
*Assistant Examiner*—Suezu Ellis
(74) *Attorney, Agent, or Firm*—O'Brien Jones, PLLC

(57) ABSTRACT

The present application relates to an apparatus and method for measuring liquid levels in small-volume wells.

20 Claims, 17 Drawing Sheets

LIQUID LEVEL MEASUREMENT

CROSS REFERENCE TO RELATED APPLICATIONS

This application claims a priority benefit under 35 U.S.C. § 119(e) from U.S. Patent Application No. 60/584,450 filed Jun. 29, 2004 and U.S. Patent Application No. 60/664,730 filed Mar. 24, 2005, both of which are incorporated herein by reference.

DESCRIPTION

1. Field

The present application relates to an apparatus and method for measuring liquid levels for small volumes in wells containing quantities in the small-volume and sub-small-volume ranges.

2. Introduction

In the biological field, small-volume wells can be used for liquid reactions, storage, and handling. In the efforts toward minituarization and parallelization of biological assays, smaller volume per reaction is desirable because of minimizing sample usage and easing sample handling. Reactions can be performed in small liquid volumes ranging from nanoliter to the microliter scale for each reaction well. Where such small-volume wells are grouped together, for example, as in a multiwell tray or tube rack, it can be desirable to determine the volume of liquid in each small-volume well. Small-volume wells are too small for presently available methods and instruments for liquid level measurement. It can be desirable to provide a non-contact, automated method for measurement of liquid levels in small-volume wells. It can also be desirable to provide method of determining liquid weight through density calculations using the measured liquid volume.

SUMMARY

In various embodiments, the present teachings can provide a method for detecting liquid level in a small-volume well including confocally measuring a first distance from a reference point to a top surface of the small-volume well, confocally measuring a second distance from the reference point to a top surface of the liquid, and determining a difference between the first distance and the second distance.

In various embodiments, the present teachings can provide a system for detecting liquid level in a small-volume well including a confocal scanner adapted to measure a first distance from a reference point to a top surface of the small-volume well and a second distance from the reference point to a top surface of the liquid, at least one linear actuator adapted to position the confocal scanner or the small-volume well in a substantially vertical direction, and a processor adapted to collect information from the first distance and the second distance measurements and to calculate the difference between the first distance and the second distance measurements.

In various embodiments, the present teachings can provide a method for detecting liquid level in a small-volume well, the method including confocally measuring a first distance from a reference point to a top surface of the small-volume well, confocally measuring a second distance from the reference point to a top surface of the liquid, and determining a difference between the first distance and the second distance, wherein the liquid level in the small-volume well cannot be measured by a level sensor.

In various embodiments, the present teachings can provide a system for detecting liquid level in a small-volume well, the system including means for measuring a first distance from a reference point to a top surface of the small-volume well and measuring a second distance from the reference point to a top surface of the liquid, means for positioning the confocal scanner in a substantially vertical direction, and means for calculating the difference between the first distance and the second distance measurements.

In various embodiments, the present teachings can provide a system for detecting liquid level in a small-volume well, the system including means for measuring a first distance from a reference point to a top surface of the small-volume well and measuring a second distance from the reference point to a top surface of the liquid, means for positioning the small-volume tube in a substantially vertical direction, and means for calculating the difference between the first distance and the second distance measurements.

DESCRIPTION OF VARIOUS EMBODIMENTS

Figure 1:
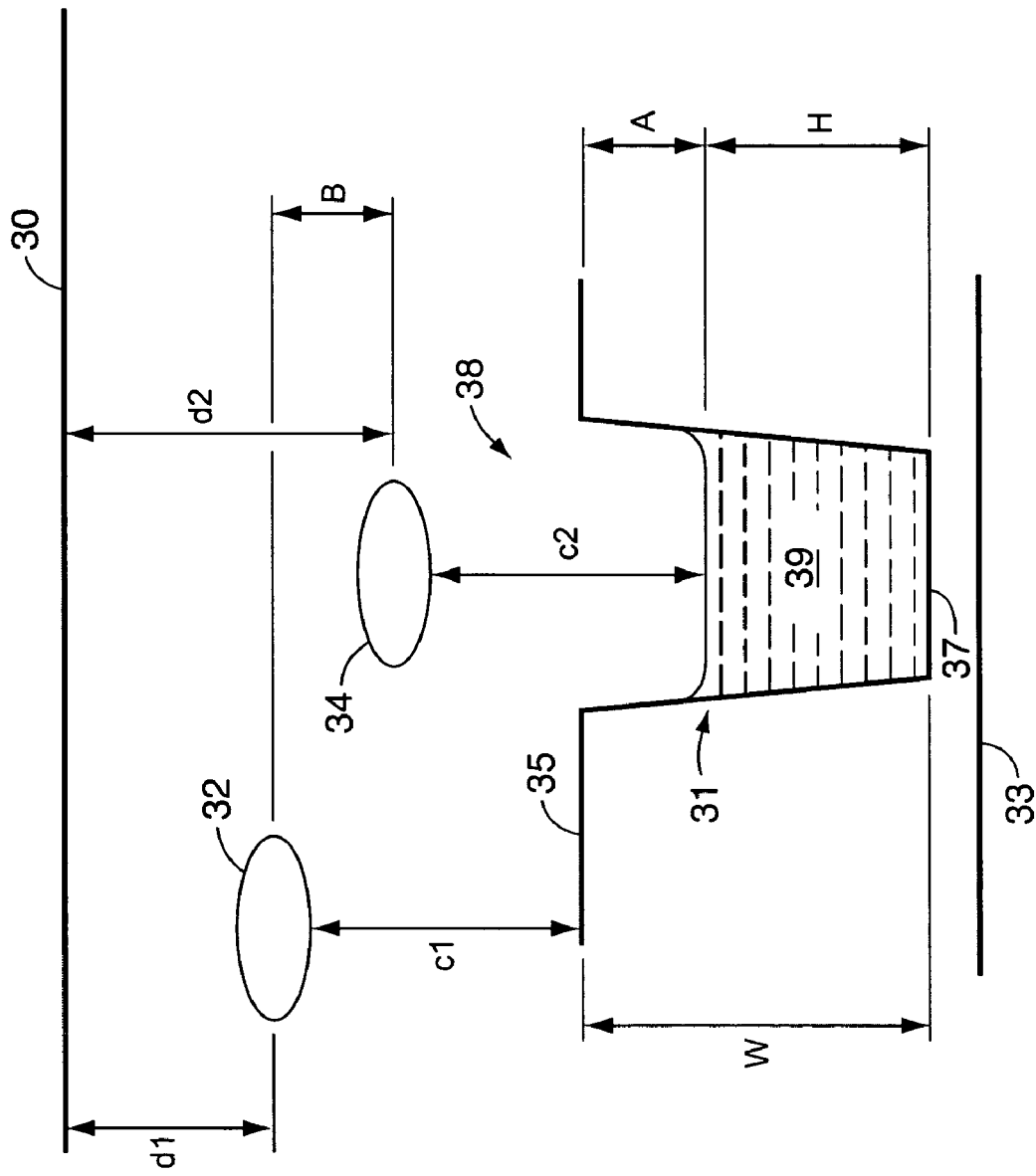
FIG. 1 illustrates a schematic view of a method for liquid level measurement according to the present teachings.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Wherever possible, the same reference numbers will be used throughout the drawings to refer to the same or like parts.

The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose.

The term "small-volume" as used herein refers to receptacles for containing liquid volumes on the order of microliters, such as less than one milliliter, or on the order of nanoliters, such as less than one microliter. As used herein the term "wells" refers to any container including a well, a tube, a capillary, a vial, a cuvette, etc. The container can have any shape including square, rectangular, circular, cylindrical, etc. The small-volume wells can be grouped together in a row (e.g. a tube strip), an array (e.g. multiwell tray), or an assembly (e.g. a carrousel). A small-volume well is too small in volume for contact methods of liquid volume measurement. The numbers of small-volume wells grouped together can range from 1,2,4,8,16,24,48,96, 384,1536, 6144, etc.

The term "confocal" and variations thereof as used herein refer to optical surface profiling based on a scanning confocal method. This confocal method uses a pin-hole or slit to obstruct the light that is not emanating from a focal plane of the light, where the unobstructed light propagates through one or a series of lenses. Light emanating from above or below the focal plane is not focused on the pin-hole or slit and is thereby not detected. The light source is scanned over a vertical axis to detect the presence of a surface along the detection path length. The light source can also be scanned over the horizontal axis to achieve an improved signal measurement through signal averaging or to perform surface topography over the scanned distance. "Confocal" as used herein does not refer to confocal microscopy.

The light source can be any of a variety of light sources including white light, halogen lamps, lasers, solid state lasers, laser diodes, micro-wire lasers, diode solid state lasers (DSSL), vertical-cavity surface-emitting lasers (VC-SEL), LEDs, phosphor coated LEDs, organic LEDs (OLED), thin-film electroluminescent devices (TFELD), phosphorescent OLEDs (PHOLED), inorganic-organic LEDs, LEDs using quantum dot technology, LED arrays, filament lamps, arc lamps, gas lamps, and fluorescent tubes. Light sources can have high irradiance, such as lasers, or low irradiance, such as LEDs. The different types of LEDs mentioned above can have a medium to high irradiance.

The detector can be any variety of detector including charged coupled devices (CCD), back-side thin-cooled CCDs, front-side illuminated CCDs, a CCD array, a photodiode, a photodiode array, a photo-multiplier tube (PMT), a PMT array, complimentary metal-oxide semiconductor (CMOS) sensors, CMOS arrays, a charge-injection device (CID), CID arrays, etc. The detector can be adapted to relay information to a data collection device for storage, correlation, and/or manipulation of data, for example, a computer, or other signal processing system.

In various embodiments, the present teachings provide methods for simultaneous measurement of two or more surface levels in one measurement, for example, the liquid level and at least one reference point. In various embodiments, two or more surface levels can be measured in two measurements, for example the plate surface and at least one reference point, and the liquid level and at least one reference point. In various embodiments, the reference point can be bottom of the well, the top surface of a cover, and/or the bottom surface of a cover. In various embodiments, the reference point can be the location of the confocal scanner relative to a measurable surface, for example, the top of the plate containing the small-volume well, the bottom of the well, the top surface of a cover, the bottom surface of a cover, and/or the top surface of the liquid.

In various embodiments, the small-volume well can be oriented such that the liquid rests at the bottom of the well. This orientation can be, for example, opening upward where gravity is forcing the liquid downward against the bottom of the well, or opening to the left where a centrifugal force or pressure force is forcing the liquid to the right against the bottom of the well, for example. In various embodiments, the small-volume well can be covered and oriented such that the liquid rests on the cover. This orientation can be, for example, opening downward where gravity is forcing the liquid downward against the cover, or opening to the left where a centrifugal force or pressure force is forcing the liquid to the left against the cover.

In various embodiments, the liquid in the small-volume well can be any type of liquid including opaque, colored, translucent, and/or clear (colorless). In various embodiments, the small-volume well can be hydrophobic or hydrophilic providing different interactions with the liquid. Such interactions can form a meniscus at the interface of the liquid and the wall of the small-volume well.

Figure 2:
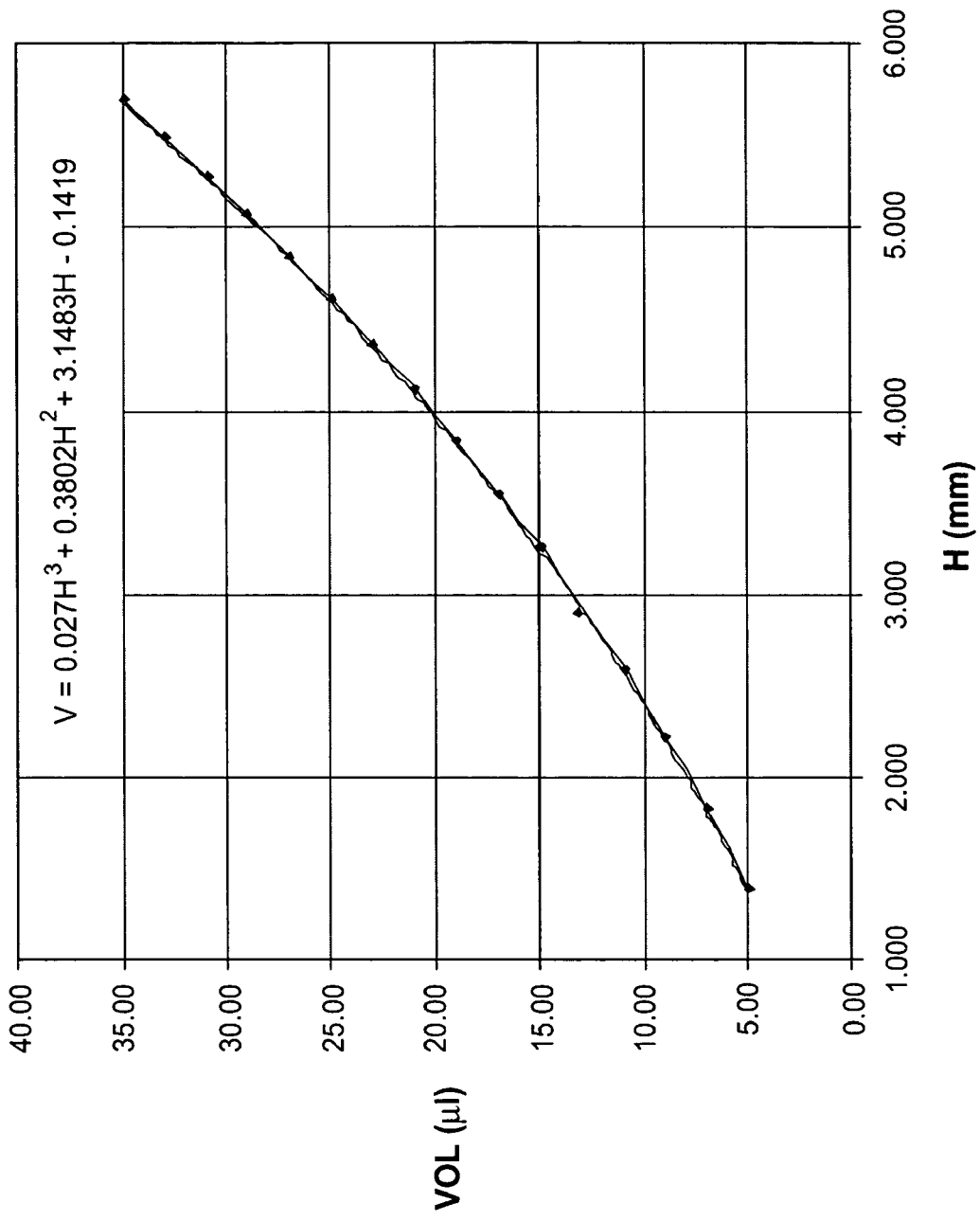
FIG. 2 illustrates a graph for calculating liquid volume from liquid level according to the present teachings.

In various embodiments, as illustrated in FIG. 1, the system for detecting liquid level in a small-volume well. Small-volume well 38 has top surface 35 and well bottom 37. If the small-volume well 38 is part of a tray or plate, it contains plate bottom 33. The confocal scanner 32, 34 can have first position at 32 and second position at 34 relative to the stage 30. The confocal scanner can maintain a uniform distance above the small-volume well 38 and liquid 39. By maintaining a uniform distance, the distance between confocal scanner at first position 32 and the top surface 35 of the small-volume well 38, designated by the value c1, and the distance between confocal scanner at second position 34 and the liquid meniscus level 31, designated by the value c2, are substantially equal to each other. The confocal scanner can be translated by a linear actuator (not shown in FIG. 1) between the first position 32 and second position 34. The difference between the distances between the stage 30 and the confocal scanner at the first position 32, designated by the value d1, and between the stage 30 and the confocal scanner at the second position 34, designated by the value d2, provides the value B, i.e., B=(d2−d1). The value B is substantially equal to A, the value representing the distance between the top surface 35 of the small-volume well 38 and the liquid meniscus level 31 of liquid 39. Since the well depth, W, is known, the height of the liquid, H, can be calculated as H=W−A. By calculating the value for H, the volume of liquid can be determined by the theoretical volume equation as a function of H for the small-volume well. The example represented in FIG. 1 has the theoretical volume equation of $V(H)=0.0208H^3+0.4059H^2+2.7428H-$ 0.9741. FIG. 2 illustrates a graph of theoretical volume of the small-volume well in microliters as a function of height in millimeters.

In various embodiments, d1 and d2 can be substantially equal and A can be calculated by the difference in c1 and c2 by translating the stage and confocal scanner. In various embodiments, d1 and d2 can be substantially equal and A can be calculated by the difference in c1 and c2 by translating the small-volume well. In each embodiment, the confocal scanner can find the focal plane of the small-volume well surface and liquid meniscus level.

In various embodiments, a method for detecting liquid level in a small-volume well can include confocally measuring a first distance, such as d1, from a reference point, such as a stage, to a top surface of the small-volume well, confocally measuring a second distance, such as d2, from the reference point, such as a stage, to a top surface of the liquid, such as by identifying the liquid meniscus level, and determining a difference between the first distance and the second distance. This can permit determining the volume of liquid in the small-volume well, by for instance, determining the height of the top surface of the liquid to the bottom of the well and calculating the volume with a formula for the volume of the small-volume well provided, such as a theoretical volume formula.

In various embodiments, a method for detecting liquid level in a small-volume well can include positioning the confocal scanner to focus on the top surface of the small-volume well and positioning the confocal scanner, the stage, and/or the small-volume well to focus on the top surface of the liquid and to focus on the top surface of the small-volume well for scanning in the focal plane. This can be repeated for a plurality of wells.

Figure 3:
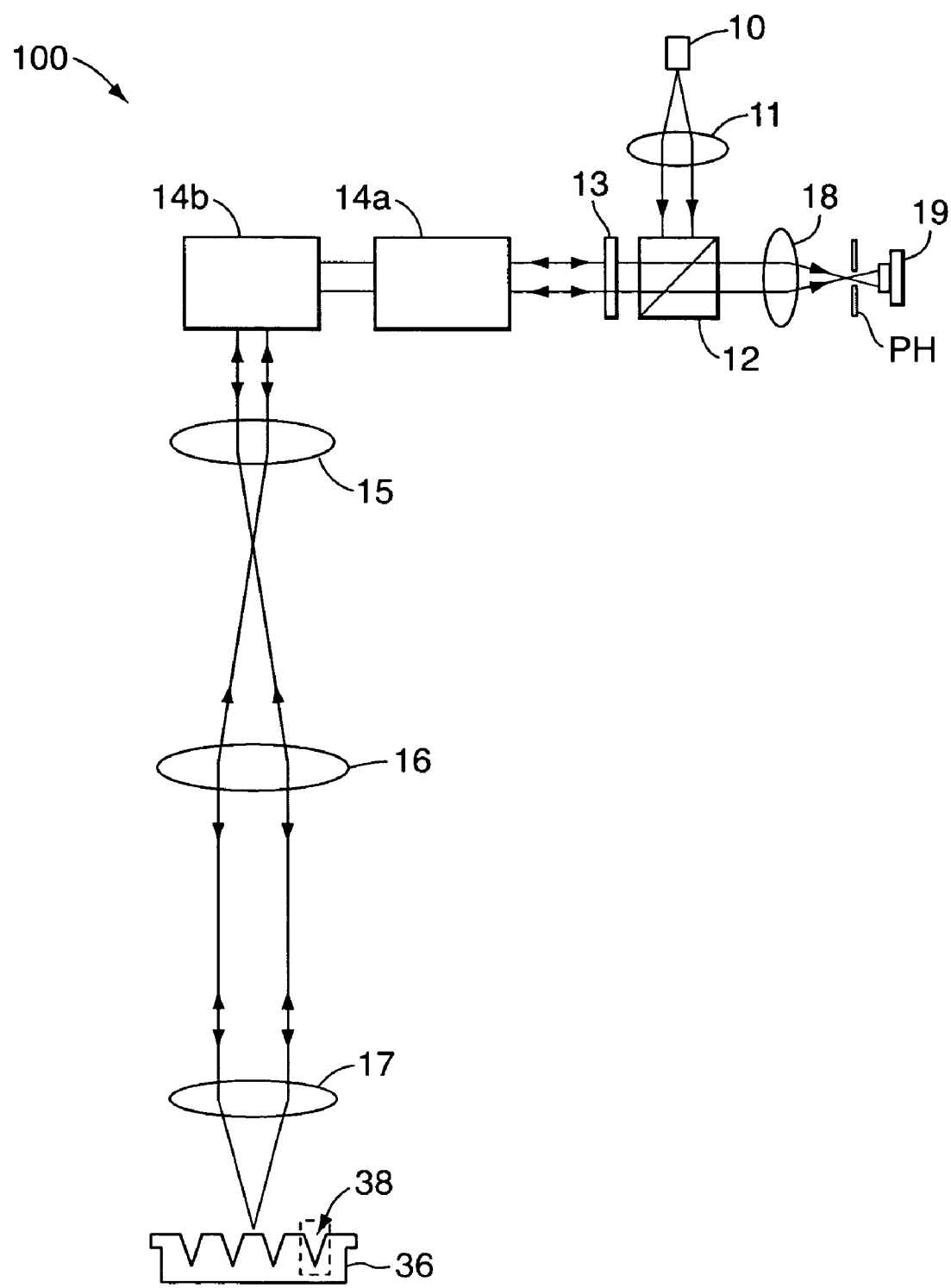
FIG. 3 illustrates a schematic for a confocal scanner according to the present teachings.
Figure 4:
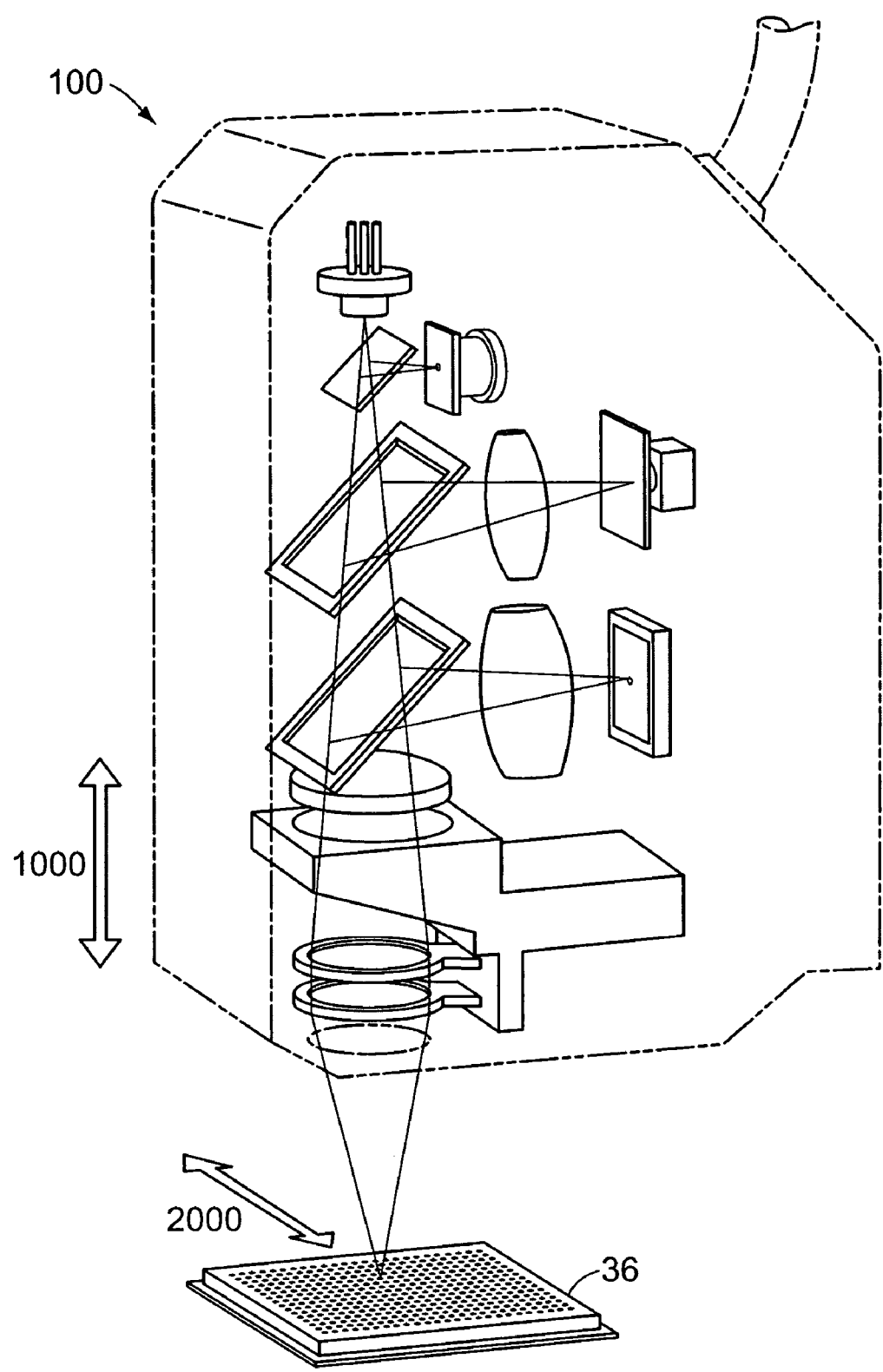
FIG. 4 illustrates a cross-sectional perspective view of an instrument for liquid level measurement according to the present teachings.
Figure 5:
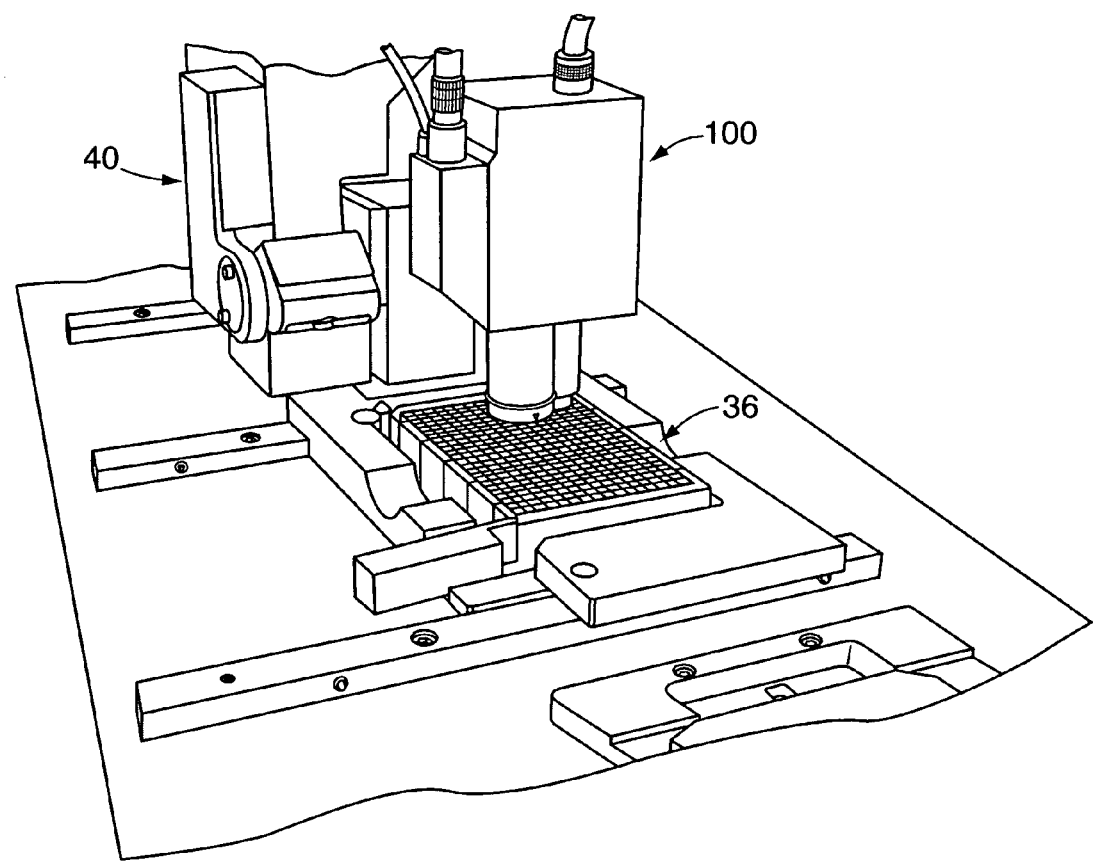
FIG. 5 illustrates a perspective view of a system for liquid level measurement of small-volume wells in a multiwell tray according to the present teachings.

In various embodiments, as illustrated in FIG. 3, confocal scanner 100 can include a variety of optical components to scan over the surface of a tray 36 with a plurality of small-volume wells 38. The optical components include light source 10, collimating lens 11, dichroic mirror 12, filter 13, scanning mechanism 14a, 14b, lenses 15, 16, 18, objective lens 17, pin hole PH, and detector 19. An example of such a confocal scanner is the LT-9000 Series manufactured by Keyence, Inc. (Japan). FIG. 4 illustrates the physical layout of the LT-9000 confocal scanner 100. The present teachings provide translating the LT-9000 vertically 1000 and laterally 2000 to measure each small-volume well in tray 36. FIG. 5 illustrates the physical layout of the system for detecting liquid level in a small-volume well showing confocal scanner 100, linear actuator 40 and tray 36 with a plurality of small-volume wells.

Figure 6:
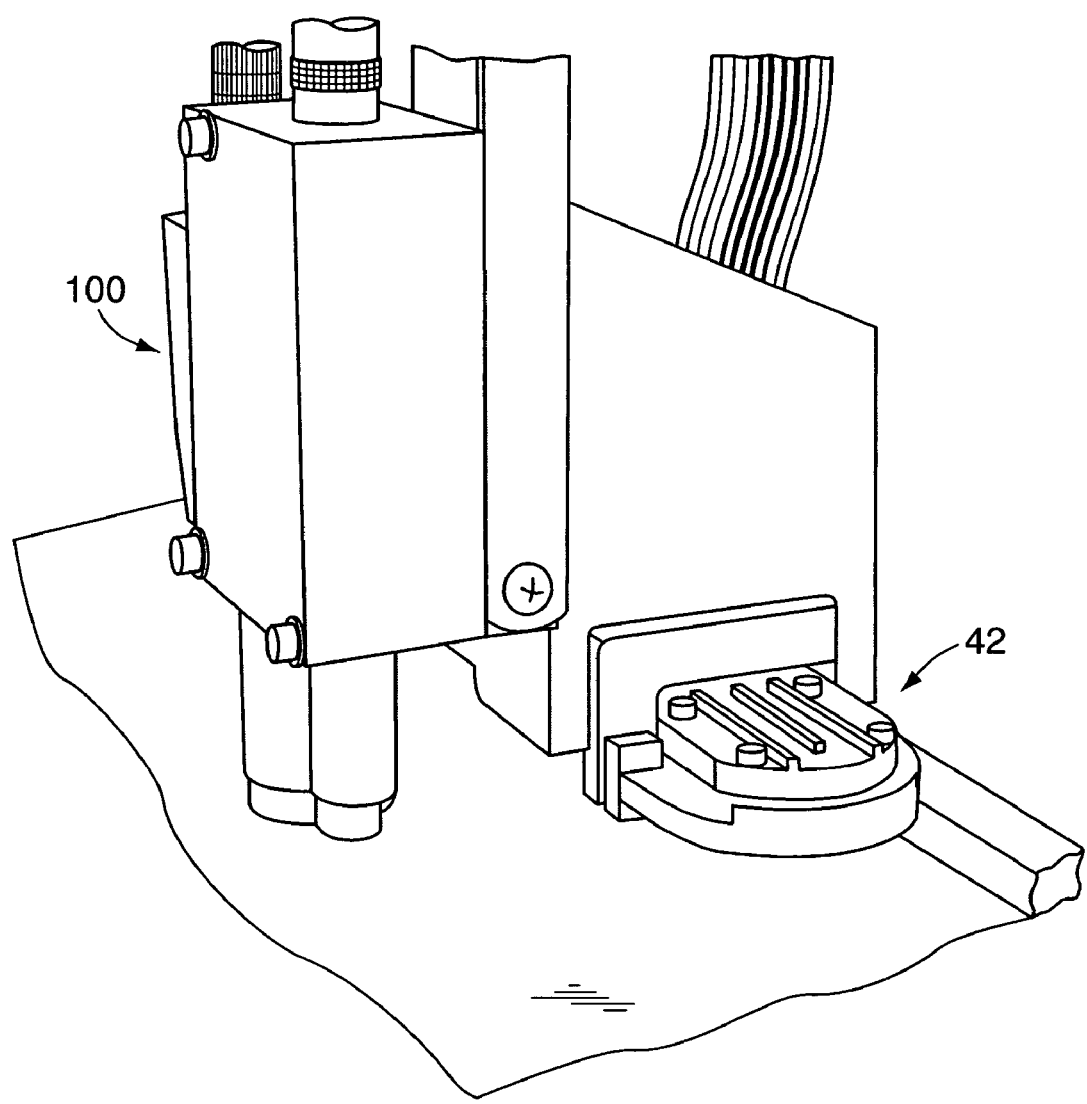
FIG. 6 illustrates a perspective view of a head for liquid level measurement and microarray spotting according to the present teachings.

In various embodiments, the liquid in the small-volume well can be depleted by liquid removed for each well and/or evaporation. This can cause a change in liquid level. An example of an application where the liquid is depleted by removal and/or evaporation is spotting a microarray with pins dipped into the small-volume wells. The success of spotting depends on sufficient liquid in each small-volume well into which a pin is dipped. In various embodiments, the liquid level can be monitored throughout the spotting process. FIG. 6 illustrates a system for detecting liquid level in a small-volume well that includes a confocal scanner 100 and pin spotting head 42 that contains a plurality of pins.

Figure 7:
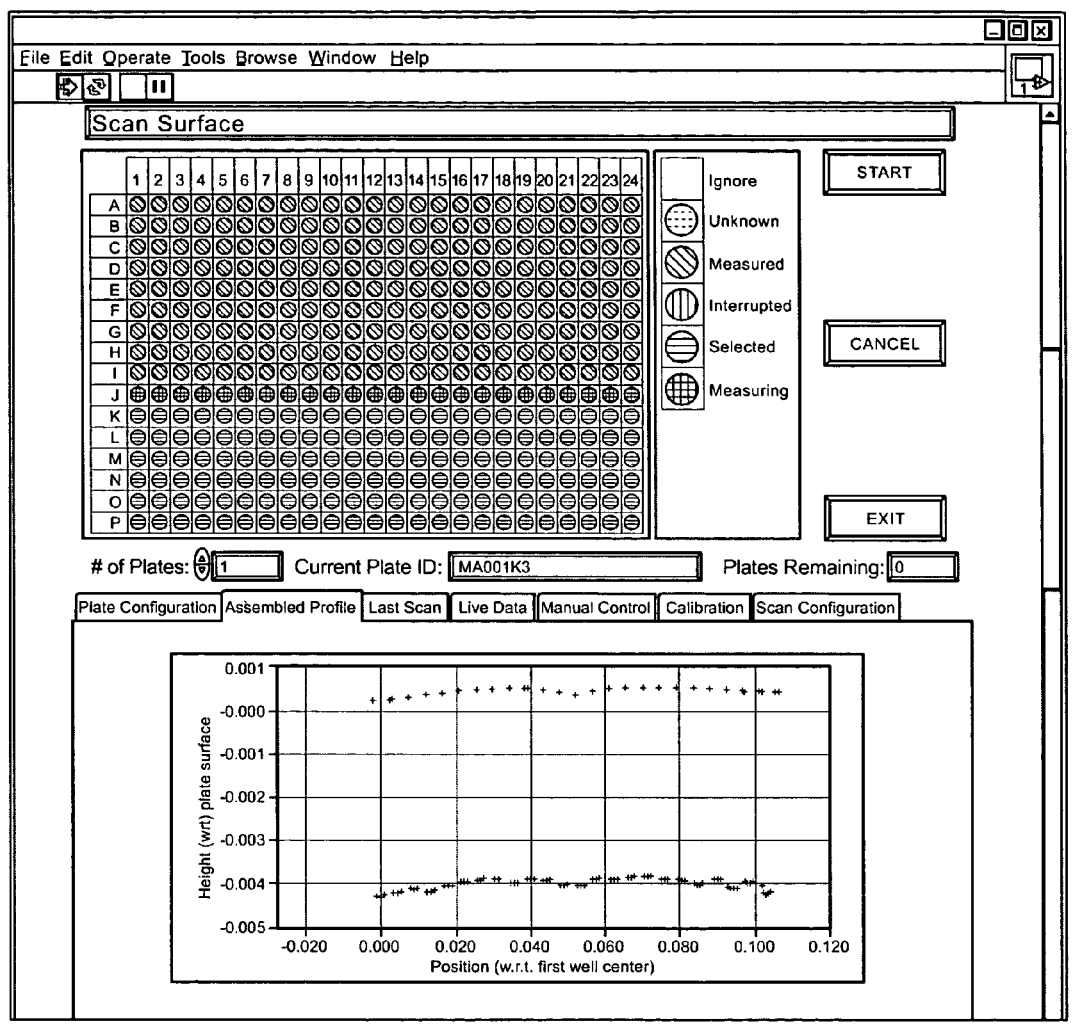
FIG. 7 illustrates a graphical user interface for software collecting liquid level measurement from a scan of all the small-volume wells in a multiwell tray according to the present teachings.
Figure 8:
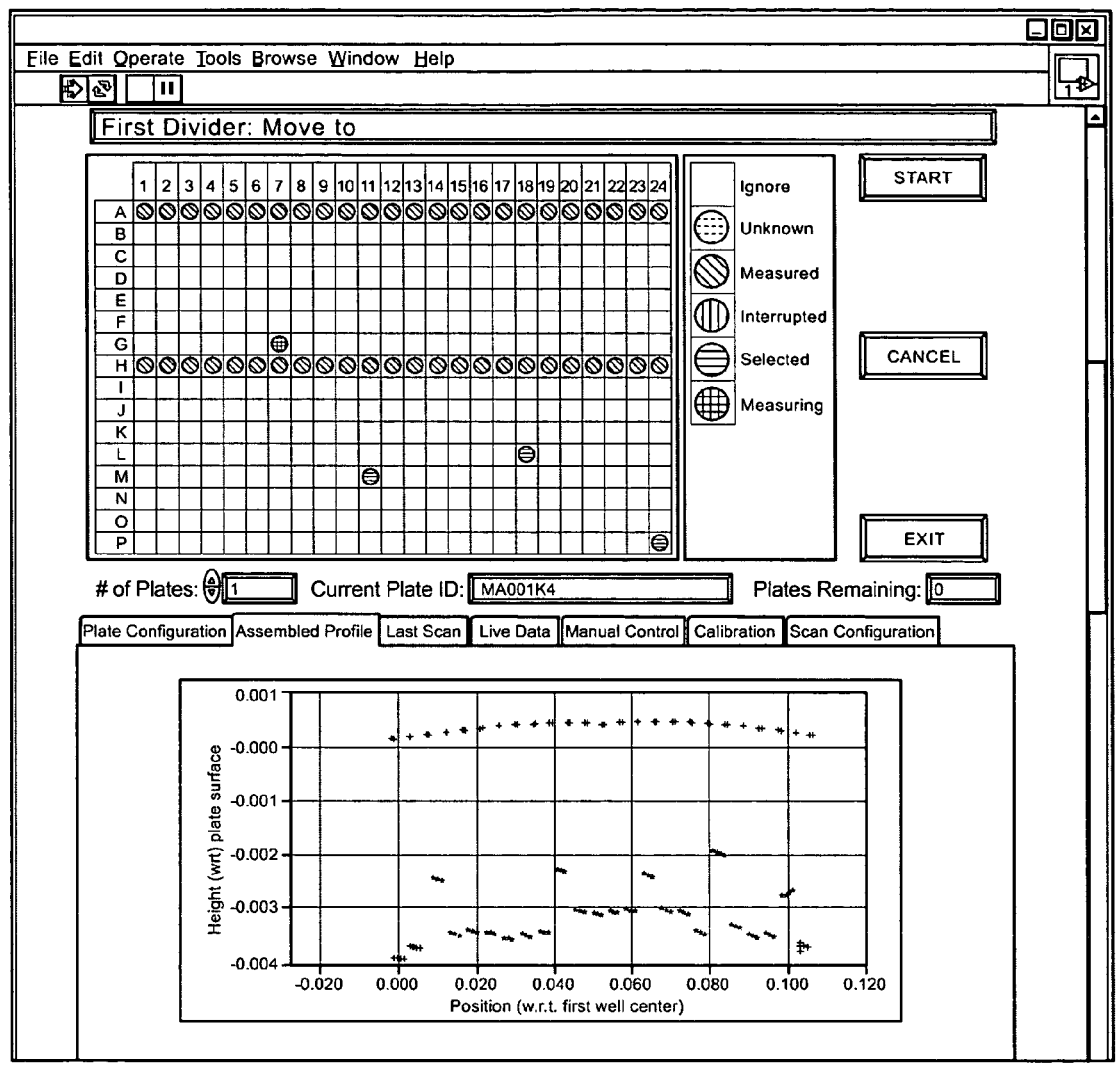
FIG. 8 illustrates a graphical user interface for software collecting liquid level measurement from a scan of selected small-volume wells in a multiwell tray according to the present teachings.

In various embodiments, as illustrated in FIGS. 7-8, software can be designed to monitor the liquid level measurements. FIG. 7 shows an example of scanning all the small-volume wells in a tray of plurality of wells. FIG. 8 shows an example of scanning selected small-volume wells in a tray of plurality of wells. Each software designates wells as "selected" as those to be measured, "measuring" as those being measured, and "measured" as those already measured. The chart on the bottom of the graphical user interface shows the height with respect to position for each small-volume well that is measured.

EXAMPLES

Figure 9A:
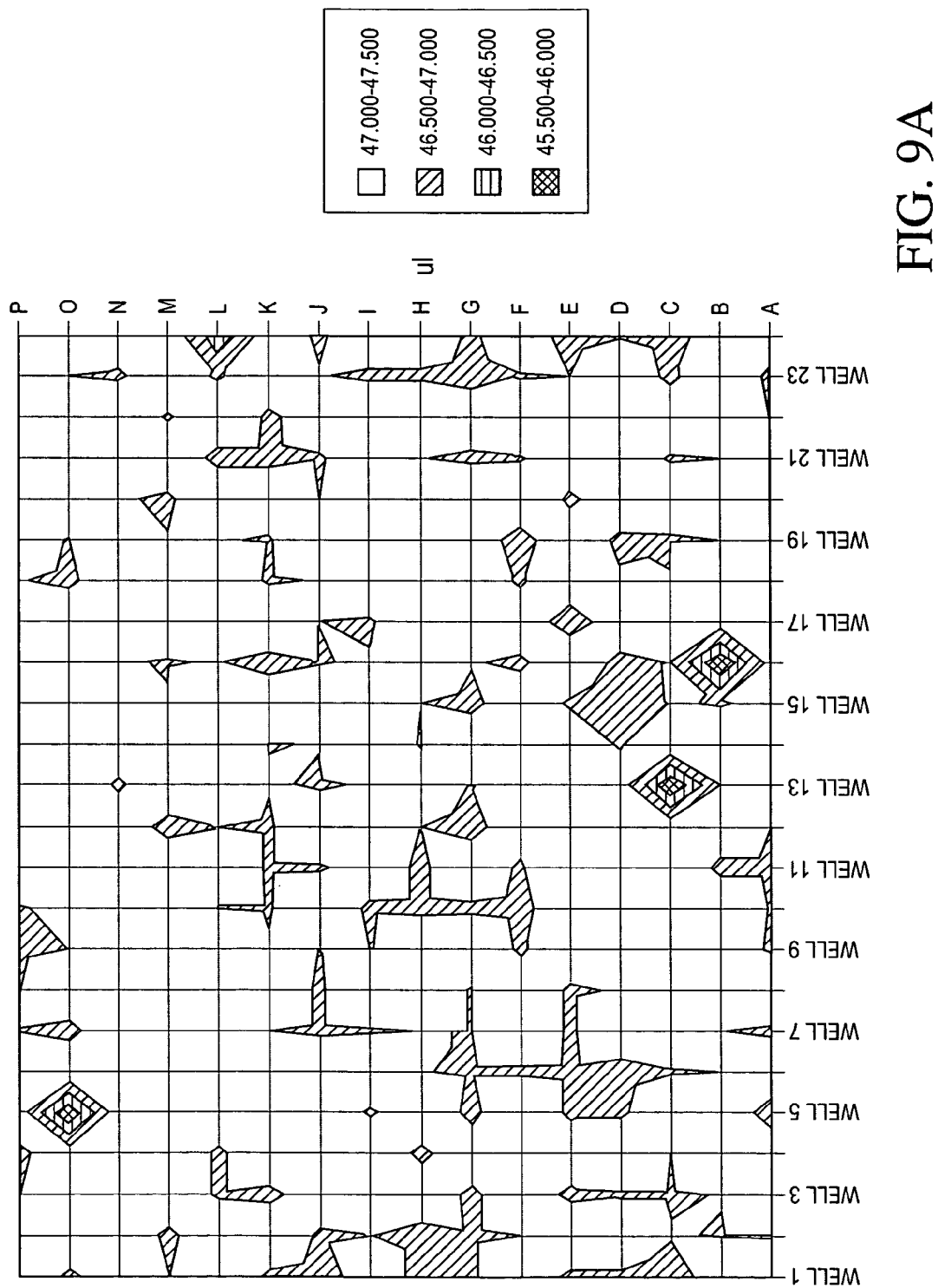
FIGS. 9A-9B illustrate a two-dimensional graph and three-dimensional graph, respectively, of the flatness of the small-volume wells in an empty 384-well plate according to the present teachings.
Figure 9B:
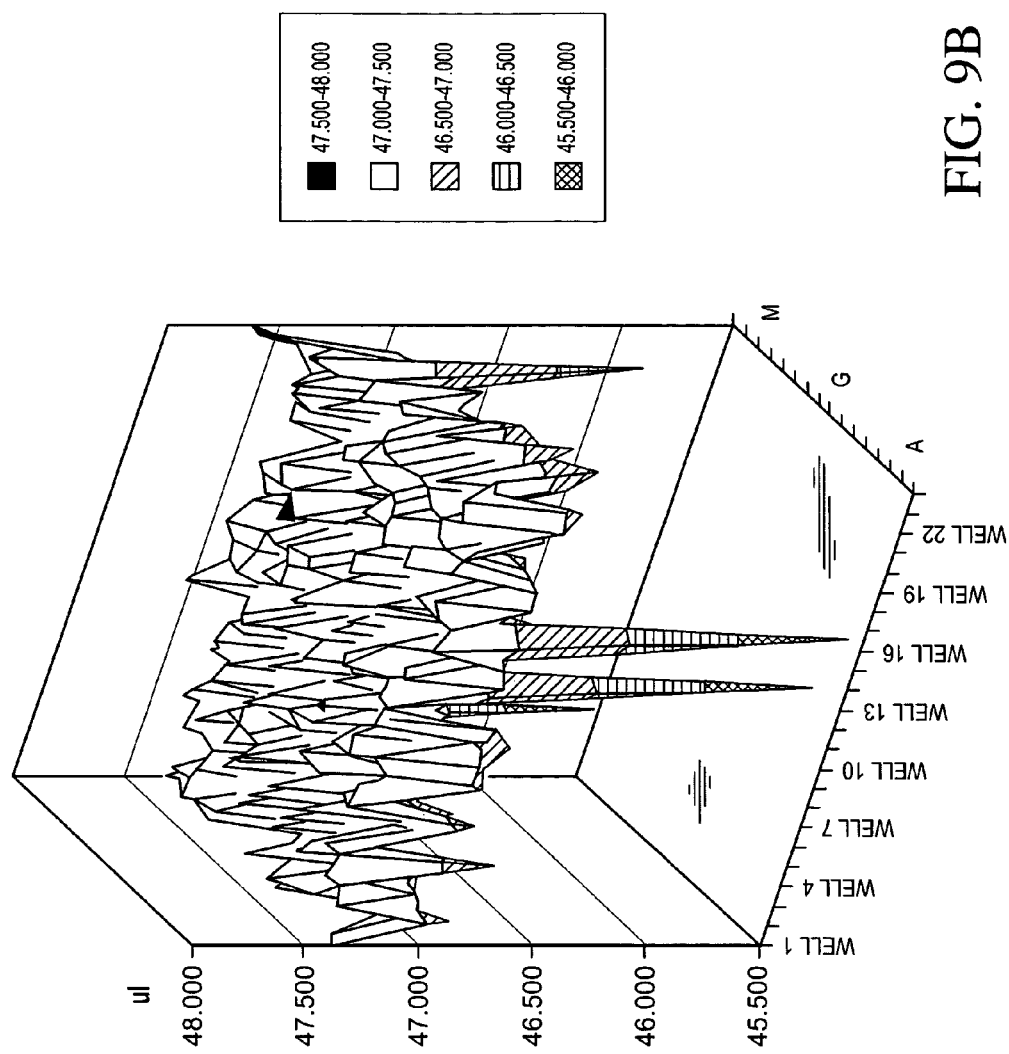

As illustrated in FIGS. 9A-9B, empty small-volume wells were measured by scanning the top surface and inside bottom of the wells. FIGS. 9A-9B illustrate a two-dimensional graph and three-dimensional graph, respectively, of the flatness of the small-volume wells in an empty 384-well plate as measured by a system described above. As the figures show, the well volume varied from 45 to 48 microliters depending on flatness.

Figure 10A:
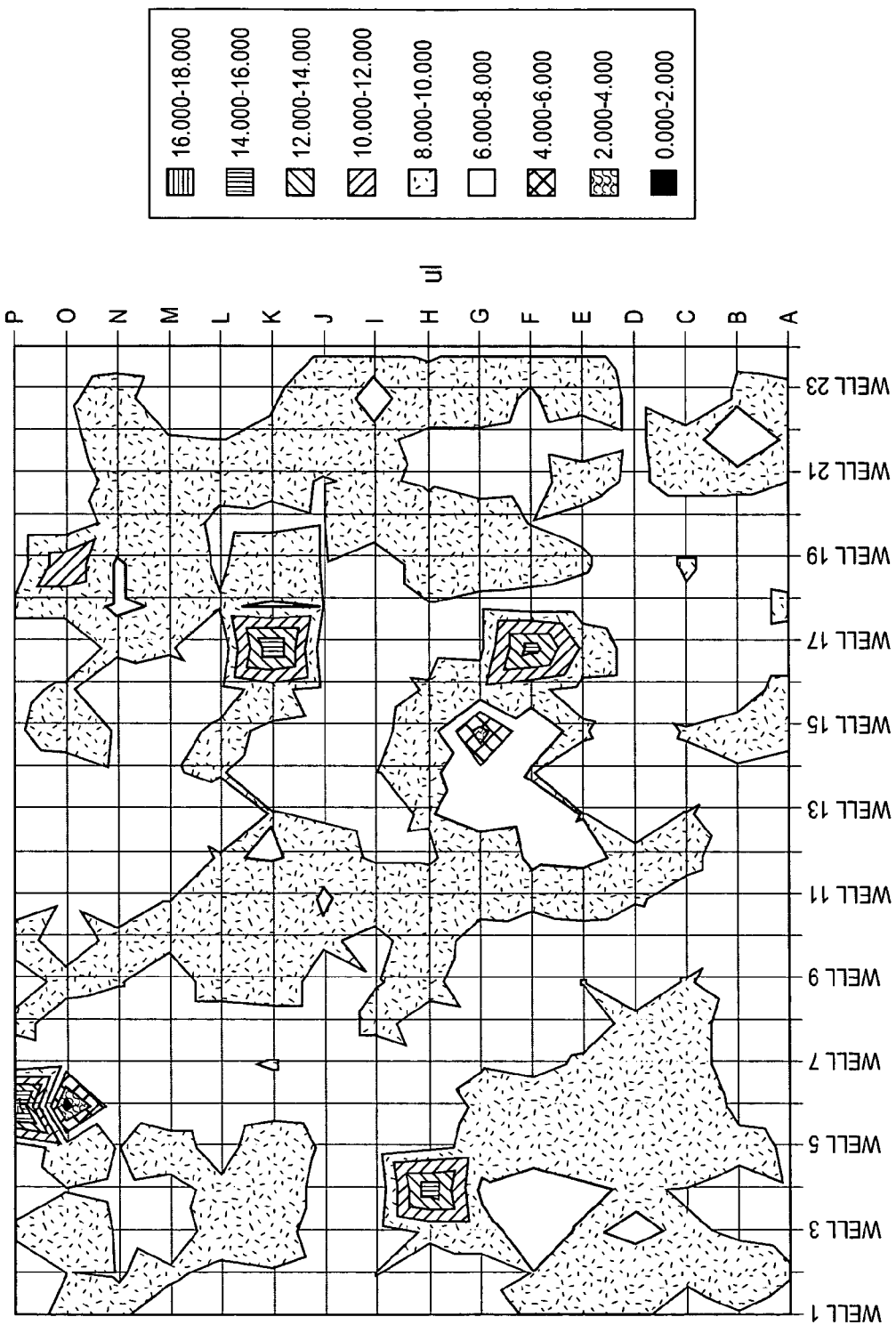
FIGS. 10A-10B illustrate a two-dimensional graph and three-dimensional graph, respectively, of the liquid volumes of a machine-pipetted 384-well plate with low liquid volumes according to the present teachings.
Figure 10B:
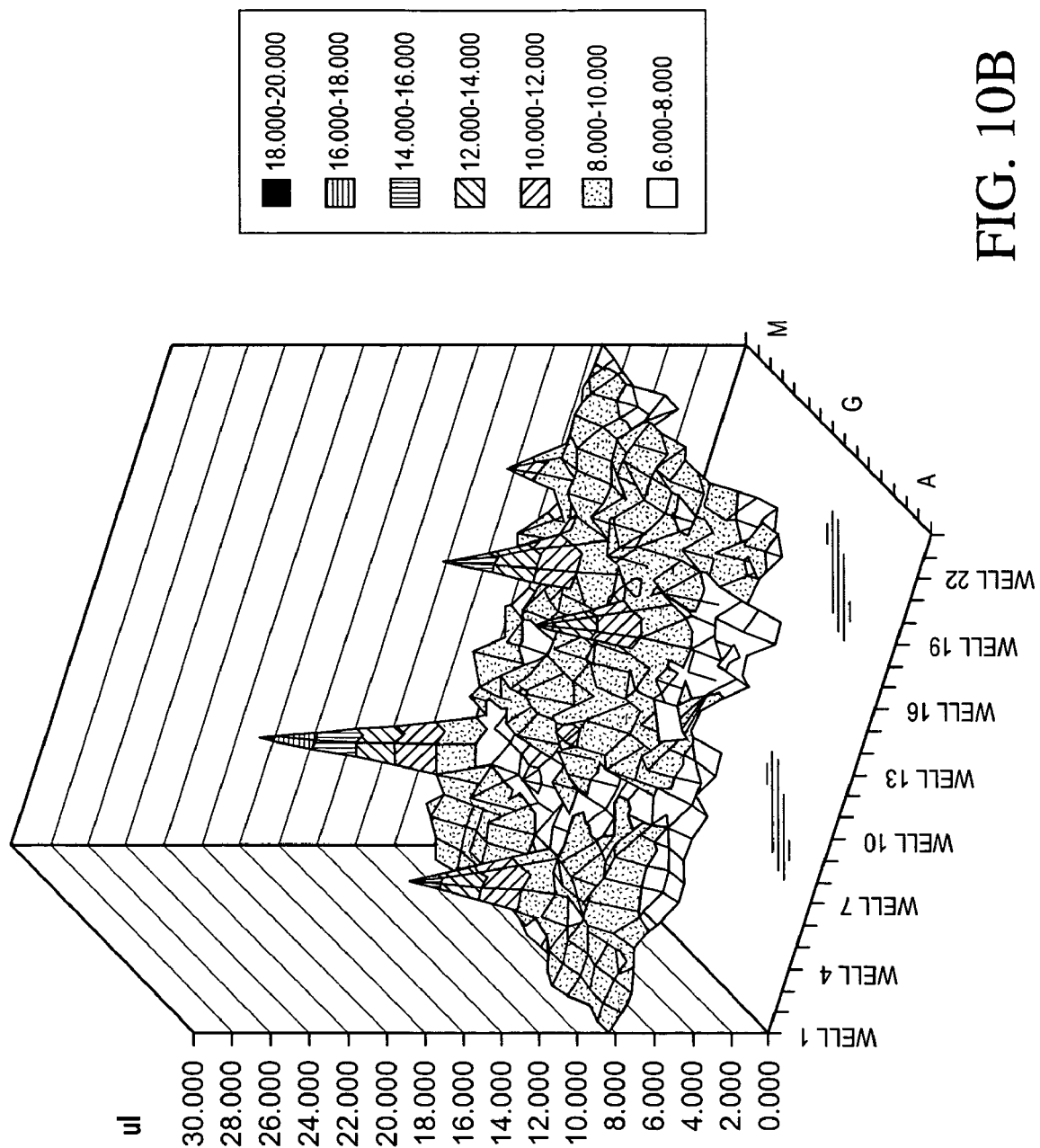

As illustrated in FIGS. 10A-10B, small-volume wells filled with relative low volumes were measured. FIGS. 10A-10B illustrate a two-dimensional graph and three-dimensional graph, respectively, of the liquid volumes of a machine-pipetted 384-well plate with low liquid volumes as measured by a system described above. The volumes averaged between 4.0 and 8.0 microliters, but varied from 2.0 to 18.0 microliters.

Figure 11:
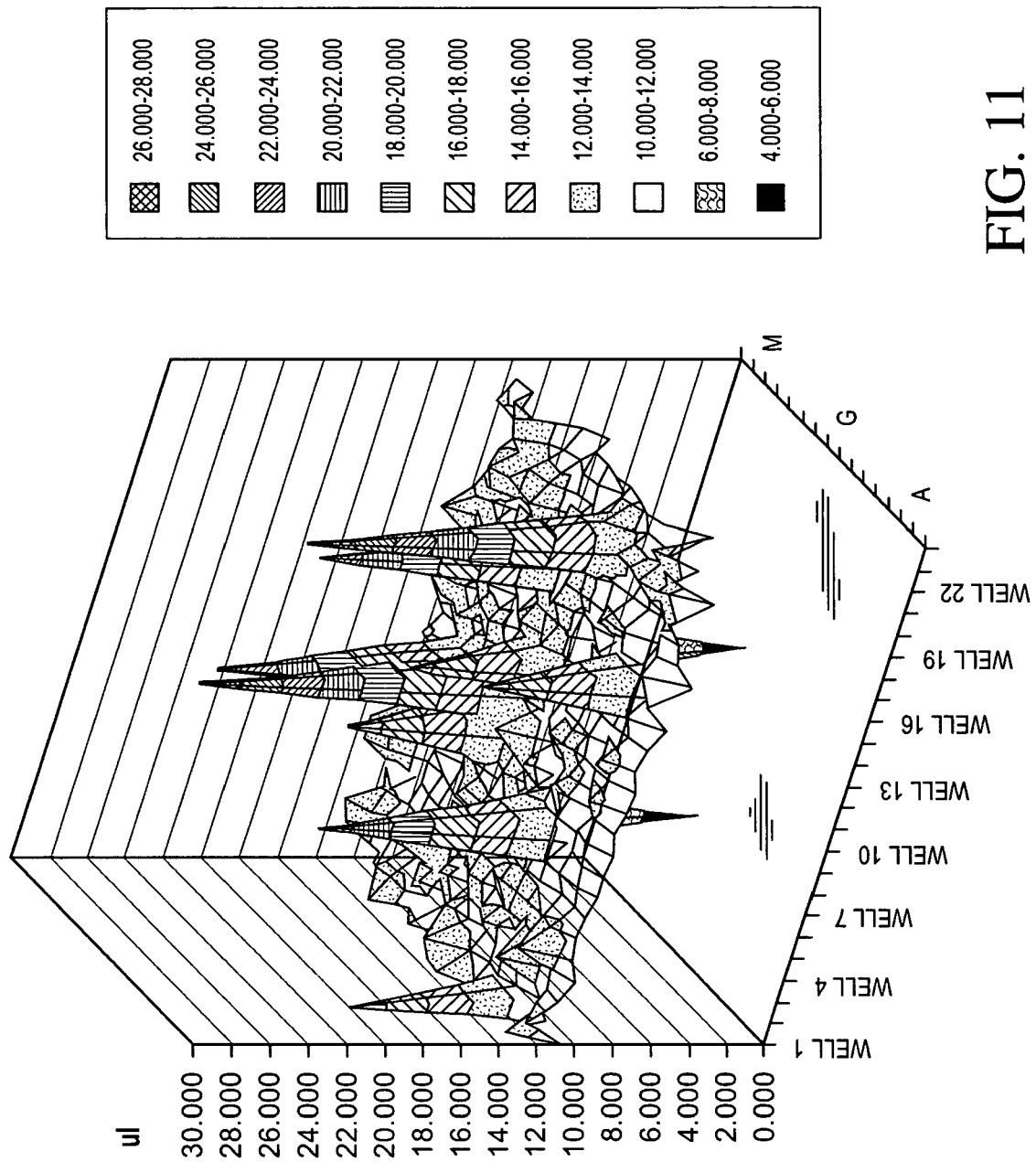
FIG. 11 illustrates a three-dimensional graph of medium liquid volumes of machine-pipetted small-volume wells in a 384-well plate according to the present teachings.

As illustrated in FIG. 11, small-volume wells filled with relatively medium volumes were measured. FIG. 11 illustrates a three-dimensional graph of medium liquid volumes of machine-pipetted small-volume wells in a 384-well plate as measured by a system described above. The volumes averaged 10.0 and 14.0 microliters, but varied from 4.0 to 28.0 microliters.

Figure 12:
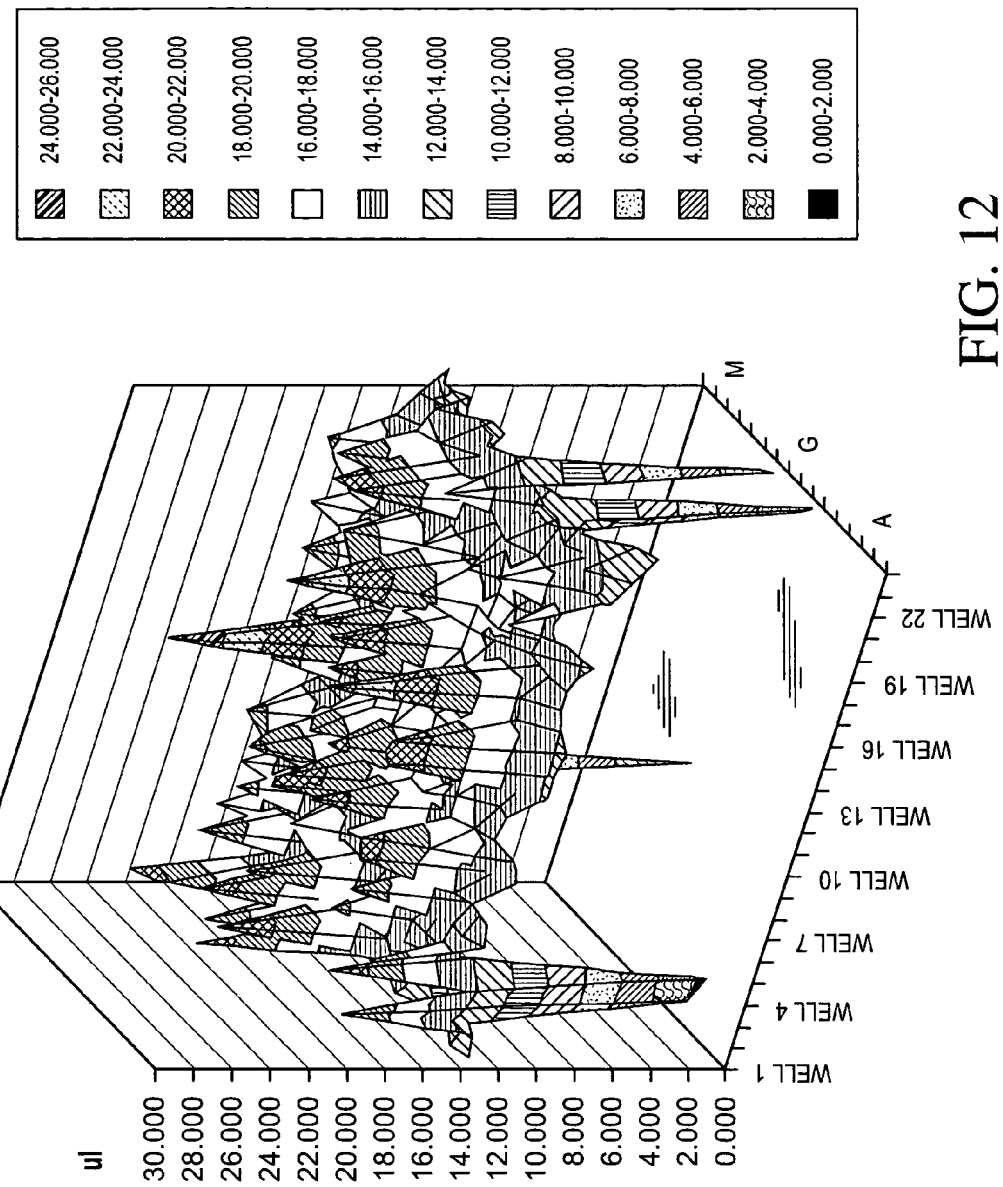
FIG. 12 illustrates a three-dimensional graph of high liquid volumes of machine-pipetted small-volume wells in a 384-well plate according to the present teachings.

As illustrated in FIG. 12, small-volume wells filled with relatively high volumes were measured. FIG. 12 illustrates a three-dimensional graph of high liquid volumes of machine-pipetted small-volume wells in a 384-well plate as measured by a system described above. The volumes averaged 14.0 to 20.0 microliters, but varied 2.0 to 26.0 microliters.

In various embodiments, the present teachings can be used to measure the liquid volumes in small-volume wells forming plates including 1536 wells, 6144 wells, 24,576 wells, 98,304 wells, etc. In such systems, the successful loading of liquid in each well can be verified by the present teachings.

Figure 13:
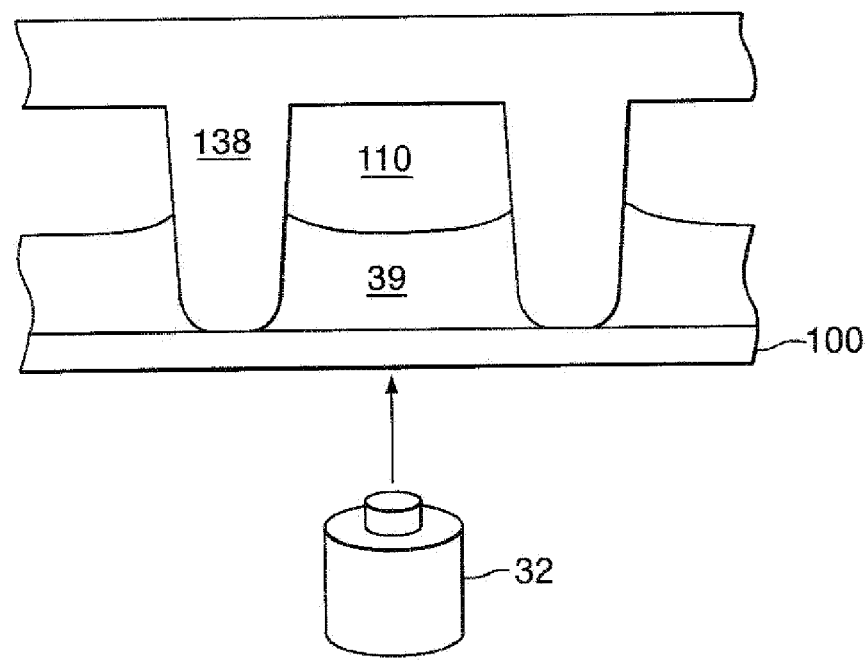
FIG. 13 illustrates a schematic view of a method for liquid level measurement according to the present teachings.
Figure 14:
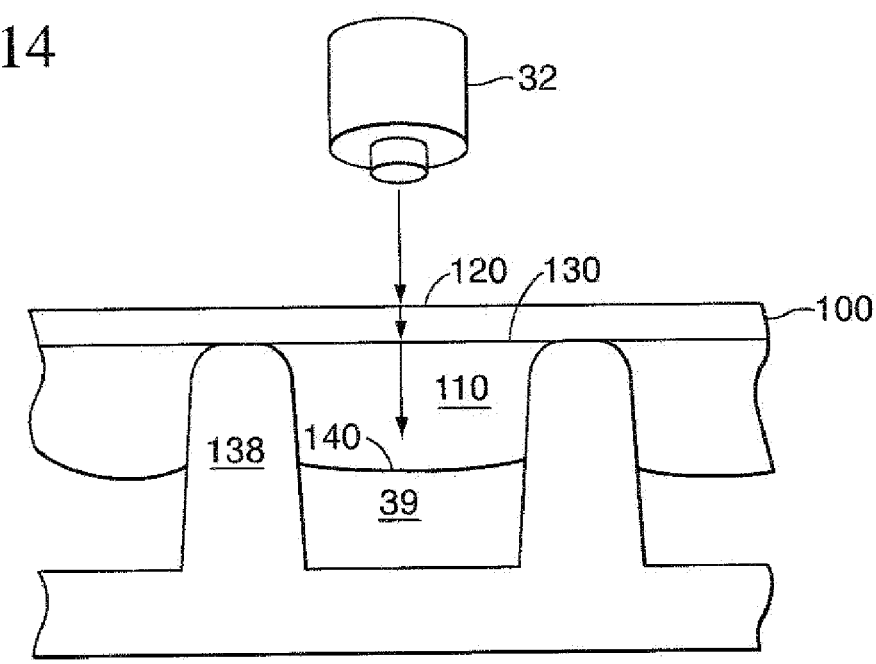
FIG. 14 illustrates a schematic view of a method for liquid level measurement according to the present teachings.

In various embodiments, FIGS. 13 and 14 illustrate methods of detecting liquid level in a small-volume well with only one point of reference by measuring the height of the liquid directly or, as described above, by measuring the void space above the liquid in the wells. The height information correlated with well dimensions provide the liquid volume in the well. In both FIGS. 13 and 14, scanner 32 can project light through cover 100 to interrogate liquid 39 positioned in a plate 138 with small-volume wells. The cover can be a transparent film or coating or a cover with an aperture or window to permit the entry and exit of light.

FIG. 13 illustrates an embodiment of the present teachings where the plate 138 is inverted such that the liquid 39 is held in the small-volume well by the cover 100. The plate 138 can be filled with spotter or loader with volumes of 150 nanoliters to 450 nanoliters. The plate 138 can be spun down in its inverted orientation to ensure the liquid 39 settles to the cover 100 pushing air gap 110 above the liquid 39. Scanner 32 provides light through cover 100 to measure the volume of liquid 39. FIG. 14 illustrates an embodiment of the present teachings wherein the plate 138 is facing upward such that liquid 39 is held in the bottom of the small-volume well. Scanner 32 provides light through cover 100 and air gap 110 to measure the volume of liquid 39. In various embodiments, there is no cover over the well. The scanner 32 can provide light to confocally detect the liquid surface level and the bottom of the well through the liquid.

In various embodiments, scanner 32 can be a laser confocal displacement meter. Such meters detect the reflection of surfaces. Such meters do not require fluorescence of the surface. An example of such as meter is LT9030M (Keyence, Japan). This meter has a height detection range of two millimeters with a scanning width range of 540 micrometers. This meter can detect four surfaces within the two-millimeter height range. As FIG. 14 illustrates, the light from scanner 32 that can reflect from the top surface 120 and the bottom surface 130 of cover 100, as well as the top surface 140 of the liquid 39. The meter can calculate the height of the void space 110 between the reflection of the bottom surface 130 of the cover 100 and the top surface 140 of the liquid 39. Such a system can operate with a single measurement to simultaneously measure surface along the height range, eliminating the need of referencing an external point or plane. In various embodiments, the meter can be stationary and the plate moved on a stage in the x-y plane to scan the small-volume wells or the plate can be stationary and the meter can be moved on a stage.

Figure 15:
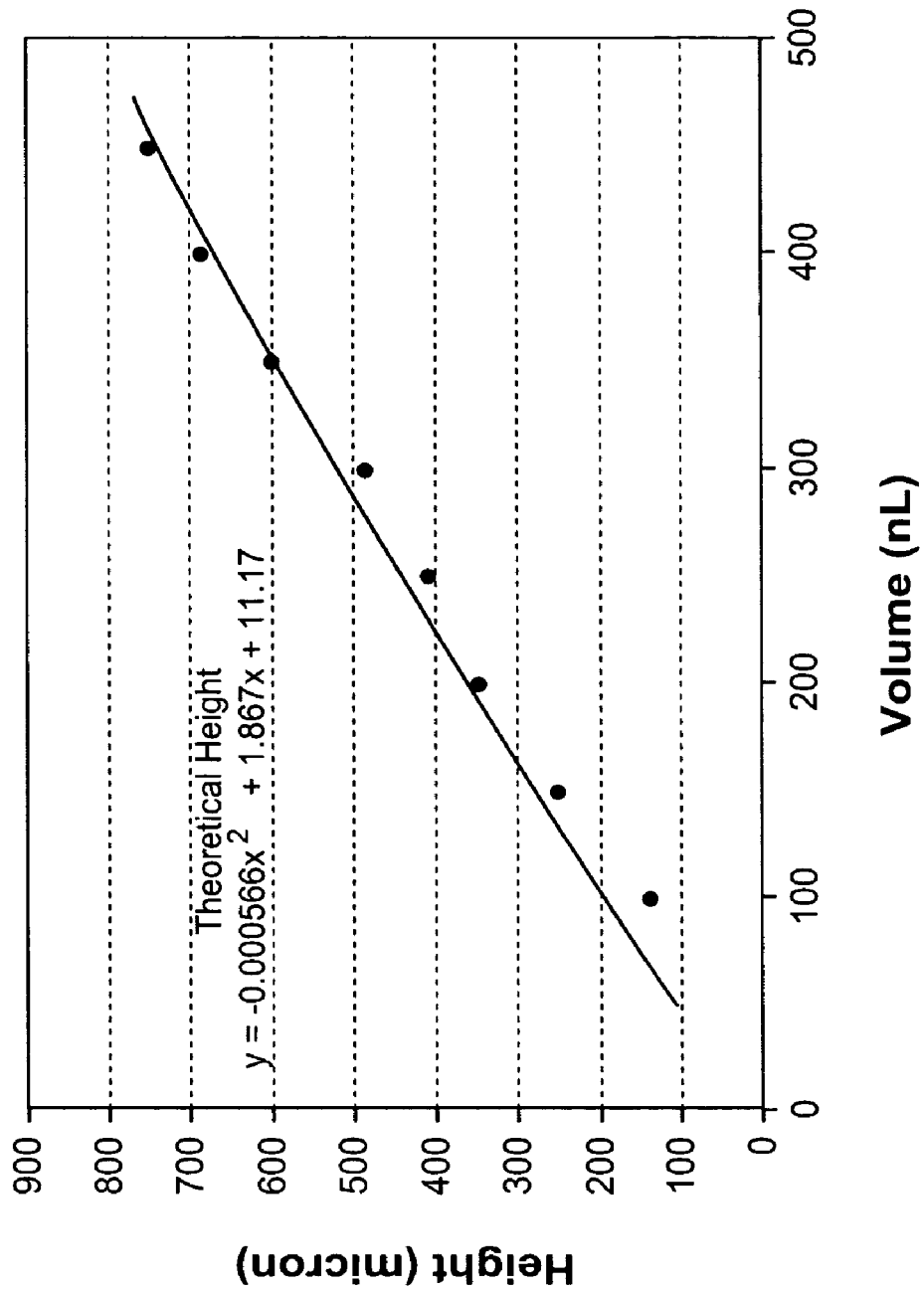
FIG. 15 illustrates a graph for calculating liquid volume from liquid level according to the present teachings.

The liquid volume can be determined by correlating the height information with well dimensions to provide the liquid volume in the well. As illustrated in FIG. 15, a plot of theoretical volume in nanoliters versus height in microns provides the comparison of height of the liquid and measured confocal height. The measured confocal height shows a correlation with varying volume. In various embodiments, the height measurement can be the average value of the surface height through scanning a specified width. In various embodiments, the height measurement can be the profile of the surface height providing the meniscus of the liquid.

In various embodiments, the scanner 32 can be a laser confocal displacement meter that can measure the liquid height in an inverted plate, as illustrated in FIG. 13. As described above, the liquid 39 sits on cover 100. Light from the meter can be reflected by the bottom surface of the liquid and the top surface of the liquid as the light can pass through the liquid.

Figure 16:
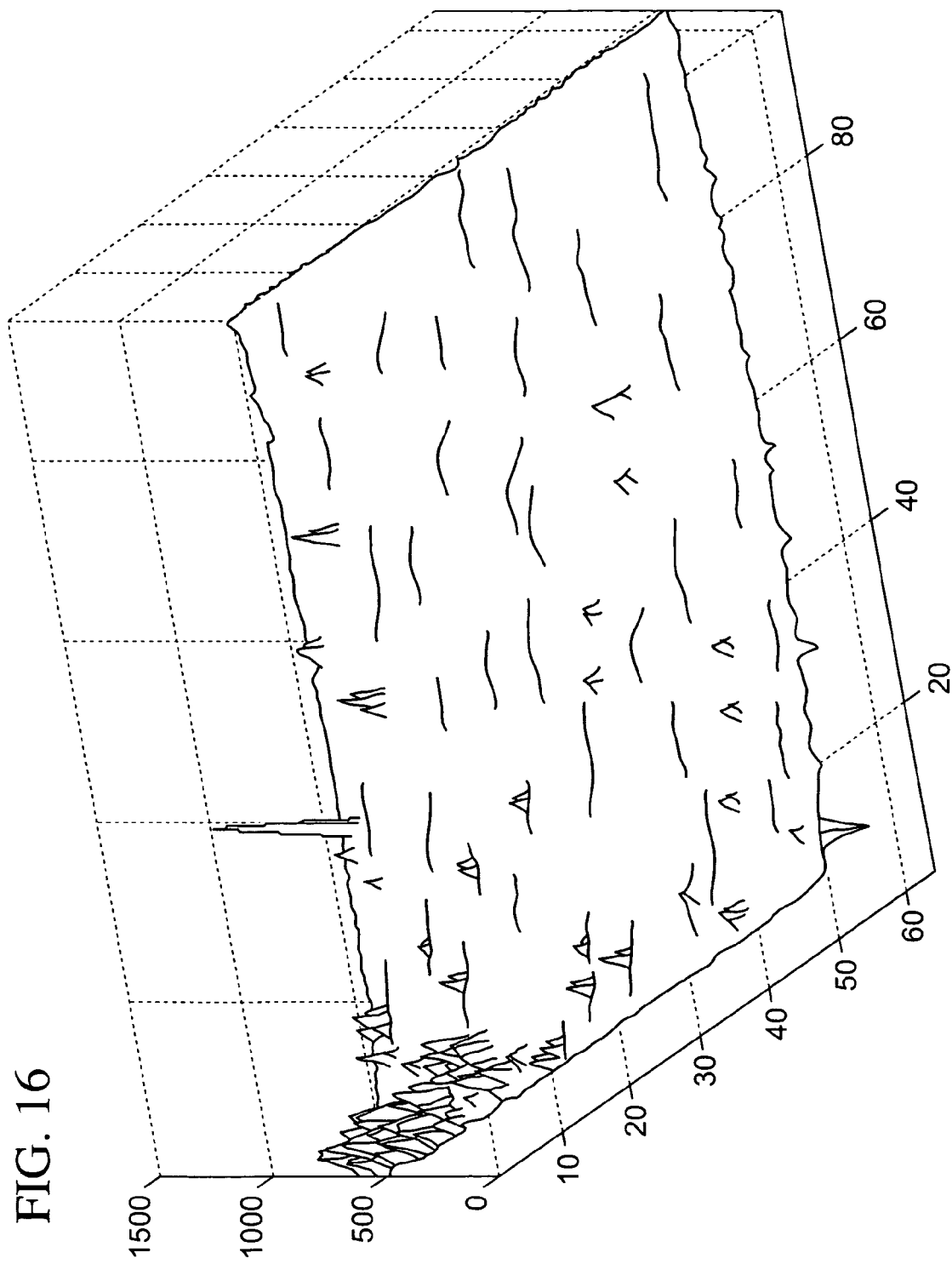
FIG. 16 illustrates a three-dimensional graph of liquid volumes of automatically pipetted small-volume wells in a 6144-well plate according to the present teachings.

In various embodiments, the movement of the scanner and/or plate can be controlled by software. In various embodiments, the software can be programmed to read in a one well at a time mode or a scanning mode. In various embodiments, the scanning mode can scan portions of the plate or the entire plate. In various embodiments, the software can be programmed to measure at the middle of the specified well. In various embodiments, the software can determine the reliability of the measurement and modify the reading location to obtain a reliable measurement. FIG. 16 illustrates the liquid volume measurements in the wells of the plate on the vertical axis with the grid of the wells on the other axes. As shown in FIG. 16, the measurements from each well in a plate can be plotted to determine whether individual wells of a plate have been properly filled with liquid.

In various embodiments, the present teachings provide measuring the top surface of the liquid, but depending on the type of liquid and the hydrophobic/hydrophilic nature of the small-volume well, or the orientation of the plate inverted or upright, a meniscus can develop causing the liquid to curve toward the scanner or away from the scanner. In such embodiments, the scanner can be used to determine the meniscus and compensate for the edge effects of the liquid against the walls of the small-volume well by factoring those into the calculation of height and/or volume.

Other various embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for detecting liquid level in a small-volume well, the method comprising:
   confocally measuring a first distance from a reference point to a top surface of the small-volume well;
   confocally measuring a second distance from the reference point to a top surface of a liquid the small-volume well;
   determining a difference between the first distance and the second distance; and
   determining a level of the liquid relative to a depth of the small-volume well based on the difference between the first distance and the second distance.

2. The method of claim 1, further comprising determining a volume of the liquid in the small-volume well.

3. The method of claim 2, wherein determining the volume of the liquid comprises determining a distance of the top surface of the liquid from a bottom of the well.

4. The method of claim 3, wherein determining the volume of the liquid further comprises providing a formula for the volume of the small-volume well.

5. The method of claim 1, further comprising adjusting a relative position of a scanner and the top surface of the small-volume well to focus the scanner on the top surface of the small-volume well and adjusting a relative position of the scanner and the top surface of the liquid to focus the scanner on the top surface of the liquid.

6. The method of claim 5, wherein adjusting the relative position of the scanner and the top surface of the liquid comprises sequentially positioning the scanner over a plurality of small-volume wells.

7. The method of claim 5, wherein adjusting the relative position of the scanner and the top surface of the liquid comprises sequentially positioning a plurality of small-volume wells under the scanner.

8. The method of claim 1, wherein determining the level of the liquid relative to the depth of the small-volume well comprises determining a distance of the top surface of the liquid from a bottom of the well.

9. A method for detecting liquid level in a small-volume well, the method comprising:
   confocally measuring a first point as a reference point;
   confocally measuring a second point at a top surface of a liquid in the small-volume well; determining a distance between the first point and the second point; and
   determining a level of the liquid relative to a depth of the small-volume well based on the distance.

10. The method of claim 9, wherein the reference point is at least one of a bottom of the well, a bottom surface of a cover on the well, and a top surface of the cover on the well.

11. The method of claim 10, wherein the first point and second point are measured substantially simultaneously without movement of a confocal scanner.

12. The method of claim 11, further comprising determining a volume of the liquid in the small-volume well.

13. The method of claim 12, wherein determining the volume of the liquid further comprises determining the volume of the liquid based on the liquid level.

14. The method of claim 13, wherein determining the volume of the liquid further comprises correlating the volume with small-volume well dimensions.

15. The method of claim 9, further comprising scanning a plate with a plurality of small-volume wells.

16. The method of claim 15, further comprising measuring one small-volume well at a time.

17. The method of claim 16, further comprising translating a confocal scanner over the plurality of wells or translating the plate with the plurality of wells under the scanner.

18. The method of claim 9, wherein the liquid is positioned at the bottom of the well.

19. The method of claim 9, wherein the liquid is retained within the well by a cover and wherein the liquid is positioned on a surface of the cover.

20. The method of claim 9, wherein confocally measuring the second point comprises determining the meniscus of the liquid.

* * * * *